(12) United States Patent
Bermudez Humaran et al.

(10) Patent No.: US 11,471,498 B2
(45) Date of Patent: Oct. 18, 2022

(54) **PROBIOTIC STRAIN OF *LACTOBACILLUS BREVIS***

(71) Applicants: INSTITUT NATIONAL DE RECHERCHE POUR L'AGRICULTURE, L'ALIMENTATION ET L'ENVIRONNEMENT, Paris (FR); INSTITUTO POLITECNICO NACIONAL (IPN), Mexico City (MX)

(72) Inventors: Luis Bermudez Humaran, Bievres (FR); Edgar Torres Maravilla, Paris (FR); Philippe Langella, Velizy (FR); Maria Elena Sanchez-Pardo, Colonia Santa Maria la Ribera Delegacion Cuauhtémoc (MX)

(73) Assignees: INSTITUT NATIONAL DE RECHERCHE POUR L'AGRICULTURE, L'ALIMENTATION ET L'ENVIRONNEMENT, Paris (FR); INSTITUTO POLITECNICO NACIONAL (IPN), Mexico City (MX)

( * ) Notice: Subject to any disclaimer, the term of this patent is extended or adjusted under 35 U.S.C. 154(b) by 0 days.

(21) Appl. No.: 15/734,375

(22) PCT Filed: Jun. 5, 2019

(86) PCT No.: PCT/EP2019/064600
§ 371 (c)(1),
(2) Date: Dec. 2, 2020

(87) PCT Pub. No.: WO2019/234076
PCT Pub. Date: Dec. 12, 2019

(65) Prior Publication Data
US 2021/0268044 A1    Sep. 2, 2021

(30) Foreign Application Priority Data
Jun. 6, 2018  (FR) ...................................... 1854912

(51) Int. Cl.
*A61K 35/747*    (2015.01)
*A23L 33/135*    (2016.01)
*C12N 1/20*    (2006.01)
*C12R 1/24*    (2006.01)

(52) U.S. Cl.
CPC .......... *A61K 35/747* (2013.01); *A23L 33/135* (2016.08); *C12N 1/205* (2021.05); *C12R 2001/24* (2021.05)

(58) Field of Classification Search
None
See application file for complete search history.

(56) References Cited

FOREIGN PATENT DOCUMENTS

EP    0 599 479 A2    6/1994
WO    99/42568 A1    8/1999

OTHER PUBLICATIONS

International Search Report dated Jul. 3, 2019, issued in corresponding International Patent Application No. PCT/EP2019/064600, field Jun. 5, 2019, 9 pages.
Written Opinion dated Jul. 3, 2019, issued in corresponding International Patent Application No. PCT/EP2019/064600, field Jun. 5, 2019, 5 pages.
Sakatani, A., et al., "Polyphosphate Derived from Lactobacillus brevis Inhibits Colon Cancer Progress Through Induction of Cell Apoptosis," Anticancer Research 36(2):1591-598, Feb. 2016.
Torres-Maravilla, E., et al., "Identification of Novel Anti-Inflammatory Probiotic Strains Isolated from Pulque," Applied Microbial and Cell Physiology 100(1):385-396, Oct. 2016.
The International Bureau of WIPO, International Report on Patentability issued in PCT/EP2019/064600, dated Dec. 8, 2020, 1 page.
European Patent Office, English Translation of the Written Opinion of the International Searching Authority issued in PCT/EP2019/064600, dated Jul. 3, 2019, 5 pages.
European Patent Office, English Translation of the International Search Report issued in PCT/EP2019/064600, dated Jul. 3, 2019, 4 pages.

*Primary Examiner* — Vera Afremova
(74) *Attorney, Agent, or Firm* — Christensen O'Connor Johnson Kindness PLLC

(57) ABSTRACT

The present disclosure relates to a new probiotic strain of *Lactobacillus brevis*, isolated from pulque and exhibiting anti-cancer properties, as well as to compositions which contain said strain.

8 Claims, 6 Drawing Sheets
Specification includes a Sequence Listing.

SEQUENCE LISTING

<160> NUMBER OF SEQ ID NOS: 1

<210> SEQ ID NO 1
<211> LENGTH: 321
<212> TYPE: DNA
<213> ORGANISM: Lactobacillus brevis

<400> SEQUENCE: 1

```
agccaagtct gatggagcat gccgcgtgag tgaagaaggg tttcggctcg taaaactctg      60
ttgttaaaga agaacacctt tgagagtaac tgttcaaggg ttgacggtat ttaaccagaa     120
agccacggct aactacgtgc cagcagccgc ggtaatacgt aggtggcaag cgttgtccgg     180
atttattggg cgtaaagcga gcgcaggcgg ttttttaagt ctgatgtgaa agccttcggc     240
ttaaccggag aagtgcatcg gaaactggga gacttgagtg cagaagagga cagtggaact     300
ccatgtgtag cggtggaatt a                                                321
```

PROBIOTIC STRAIN OF *LACTOBACILLUS BREVIS*

The present invention concerns a new probiotic strain of *Lactobacillus brevis*, isolated from pulque, exhibiting anti-cancer properties, as well as compositions comprising said strain.

According to the definition currently permitted, probiotics are "living organisms which, when they are ingested in a sufficient quantity, exercise positive effects on health". The probiotic organisms used in human food are generally lactic bacteria, belonging mainly to the *Lactobacillus* and *Bifidobacterium* types. The beneficial effects of probiotic bacteria are not however common to all bacteria of one same type, nor even of one same species, and are only encountered, most often, in certain strains. Furthermore, the effects observed can vary from one probiotic strain to the other, including inside one same species. Currently, the probiotic potential of lactic bacteria isolated from traditional fermented products generates a strong interest, in particular in developing countries where access to probiotics is limited and where the development of new products and food supplements could allow to fight against certain diseases (Vinderola et al., LWT-Food Sci Technol 41:1678-1688, 2008).

Pulque is a traditional Mexican alcoholic drink, resulting from the fermentation of the juice of various agaves, which contains a large diversity of lactic bacteria, in particular *lactobacillus* and leuconostocs (Escalante et al., Int J Food Microbiol 24:126-134, 2008). Recent studies suggest that certain prehispanic cultures from Mexico practiced enemas by using pulque to combat diseases and disorders with the digestive system (Lemus-fuentes, Temas de Ciencia y Technologia 102:143-150, 2006). Moreover, it has also been experimentally demonstrated that certain strains of *lactobacillus* (in particular, strains of *Lactobacillus san franciscensis*, *Lactobacillus plantarum* and *Lactobacillus composti*) isolated from pulque have anti-inflammatory properties, potentially beneficial for the treatment of intestinal inflammatory diseases (Torres-Maravilla et al., Appl Microbiol Biotechnol 100:385-396, 2015).

In this context, the inventors have succeeded in isolating a new strain of *Lactobacillus brevis* having anti-cancer properties. Surprisingly and unexpectedly, the inventors have thus shown that said strain is capable of reducing the proliferation of tumour cell lines and of modifying the expression of certain proapoptotic genes or certain genes involved in tumoral development.

The present invention thus aims for this strain of *Lactobacillus brevis*, filed according to the Budapest Treaty, with CNCM (French National Collection of Microorganism Cultures, 25 rue du Docteur Roux, 75724 Paris Cedex 15) on 30 May 2018 under number I-5321.

The strain CNCM I-5321 has been identified as belonging to the species *L. brevis* thanks to an API 50 CHL test and by sequencing of the RNA 16S.

TABLE 1

Partial sequence of the RNA 16S of the strain CNCM I-5321.

| Partial sequence of the RNA 16S of the strain CNCM I-5321 (SEQ ID NO: 1) | AGCCAAGTCTGATGGAGCATGCCG CGTGAGTGAAGAAGGGTTTCGGCT CGTAAAACTCTGTTGTTAAAGAAG AACACCTTTGAGAGTAACTGTTCA AGGGTTGACGGTATTTAACCAGAA AGCCACGGCTAACTACGTGCCAGC AGCCGCGGTAATACGTAGGTGGCA AGCGTTGTCCGGATTTATTGGGCG TAAAGCGAGCGCAGGCGGTTTTTT AAGTCTGATGTGAAAGCCTTCGGC TTAACCGGAGAAGTGCATCGGAAA CTGGGAGACTTGAGTGCAGAAGAG GACAGTGGAACTCCATGTGTAGCG GTGGAATTA |

This strain presents the following morphological and biochemical features:

Morphology: Positive Gram microorganism, bacillus form,

Metabolism: Catalase (−), heterofermentative,

Sugar fermentation: L-arabinose (+), ribose (+), D-xylose (+), D-glucose (+), D-fructose (+), D-mannose (+), A-methyl-deglucoside (+), N acetyl glucosamine (+), esculin (+), cellobiose (+), maltose (+), melibiose (+), gluconate (+), ceto-gluconate (+).

On the other hand, it has anti-cancer properties, translating itself by a capacity to inhibit the proliferation of tumour cell lines and to modify the expression of certain proapoptotic genes or certain genes involves in tumoral development.

As shown in the examples, the anti-cancer properties of the strain CNCM I-5321 are independent of its state of viability. Consequently, the present invention comprises the strain CNCM I-5321, whatever its state of viability, not only in living form, but also in dead form, in inactivated form, or also in bacterial lysate form.

In particular, the strain CNCM I-5321 can be in exponential growth or stationary phase, preferably in exponential phase.

In the present invention, a bacterium is considered as living if it is capable of multiplying. Conversely, a bacterium is considered as dead or inactivated when it has lost its capacity to multiply. Techniques allowing to inactivate bacteria are well-known to a person skilled in the art. In a non-limiting manner, the strain CNCM I-5321 can be inactivated by exposure to an ultraviolet radiation or by heating. For example, the strain CNCM I-5321 can be inactivated according to the method described in Neyzi et al., In Vitro Cell. Dev. Biol.-Animal 53:12-19, 2017. Briefly, the bacterial culture is centrifuged for 10 minutes, then the cell pellet is resuspended in PBS and exposed to UV radiation for 15 minutes in order to inactivate the bacterium. To ensure that the bacterium is no longer capable of multiplying, a control culture is produced in MRS after the UV treatment.

The present invention also encompasses strains likely to be obtained by mutagenesis or by genetic transformation of the strain CNCM I-5321. Methods allowing to mutate or to transform the strain CNCM I-5321 are well-known to a person skilled in the art and correspond to the methods routinely used to modify the genome of lactic bacteria, in particular bacteria belonging to the species *Lactobacillus brevis*. In a non-limiting manner, such methods include random mutagenesis (for example, using UV radiation or a mutagenic chemical agent), the directed mutagenesis or the homologous recombination.

Preferably, these strains conserve at least the anti-cancer properties of the strain CNCM I-5321. These can be strains, wherein one or more of the genes of the strain CNCM I-5321 has/have been mutated, for example, in order to modify certain metabolic properties (for example, the capacity of this strain to resist acidity, to resist the intestinal transit, to metabolise certain sugars, etc.). These can also be strains resulting from the genetic transformation of the strain CNCM I-5321 by one or more gene(s) of interest, allowing for example, to give to said strain, additional physiological features or to express proteins of interest that are sought to administer by way of said strain.

The present invention also aims for a cell fraction which could be obtained from the strain CNCM I-5321.

In particular, it can be a bacterial wall preparation obtained from a culture of said strain. More specifically, it can be a peptidoglycan preparation obtained from said strain. These can also be culture supernatants or fractions of these supernatants.

The cell fractions can be prepared according to methods known to a person skilled in the art. In a non-limiting manner, these methods generally comprise a step of lysing the bacteria obtained after culture and a step of separating the fractions containing the membranes of said bacteria of the total lysate obtained after the lysis step, in particular by centrifugation or filtration. For example, the cell fractions can be prepared by sonification according to the method described in Tiptiri-Kourpeti et al., PLOS one 11(2): e0147960, 2016.

In another aspect, the present invention concerns the strain *L. brevis* CNCM I-5321 or a cell fraction of said strain for its use as medicament.

Preferably, the strain CNCM I-5321 or a cell fraction of the strain CNCM I-5321 is ingested orally or via mucosal administration, in particular intranasally.

In an embodiment, the strain *L. brevis* CNCM I-5321 or a cell fraction of this is administered daily to the patient.

In an embodiment, the strain *L. brevis* CNCM I-5321 or a cell fraction of this is administered at least once a day.

In an embodiment, the strain *L. brevis* CNCM I-5321 or a cell fraction of this is administered at least once a week.

In another aspect, the present invention relates to the strain *L. brevis* CNCM I-5321 or a cell fraction of said strain for its use in preventing and/or treating cancer, in particular bowel cancer, more specifically colorectal cancer, but also other types of carcinomas such as breast cancer, lung cancer, liver cancer, etc.

As shown in the examples, the inventors have highlighted that the strain of the invention inhibits the proliferation of tumour cell lines, in particular human lines HT29, HTC116 and Caco2 derivatives of colorectal adenocarcinoma cells.

In an embodiment, the present invention relates to the strain *L. brevis* CNCM I-5321 or a cell fraction of said strain for its use such as defined above, wherein said strain inhibits the proliferation of cancer cells.

In an embodiment, the present invention relates to the strain *L. brevis* CNCM I-5321 or a cell fraction of said strain for its use such as defined above, wherein said strain or the cell fraction of said strain increases the expression of at least one proapoptotic gene in said cancer cells.

Preferably, said proapoptotic gene is chosen from among the group of genes comprising CASP8, CASP9, BCL2, BAX and BCL-XL.

In an embodiment, the present invention concerns the strain *L. brevis* CNCM I-5321 or a cell fraction of said strain for its use such as defined previously, wherein said strain or cell fraction of said strain decreases the expression of at least one gene involved in the development of a tumour.

Preferably, said gene involved in the development of a tumour is chosen from among the group of genes comprising erbB2, erbB3 and PKM2.

In another aspect, the present invention concerns a treatment method in a subject in need comprising the administration of the strain *L. brevis* CNCM I-5321 or of a cell fraction of said strain on said subject.

The present invention also concerns a method for treating cancer in a subject in need comprising the administration of the strain *L. brevis* CNCM I-5321 or of a cell fraction of said strain on said subject.

In another aspect, the present invention concerns the use of the strain *L. brevis* CNCM I-5321 or of a cell fraction of said strain for preparing a medicament.

The present invention also concerns the use of the strain *L. brevis* CNCM I-5321 or of a cell fraction of said strain for preparing a medicament intended for the treatment of cancer.

In another aspect, the present invention relates to a composition comprising the strain *L. brevis* CNCM I-5321 or of a cell fraction of it.

In a non-limiting manner, a composition according to the invention can be liquid or solid and presented itself in different forms, like for example a capsule, a lozenge, a tablet, a pill, a suppository, a sachet of powder, a liquid vial, an ampoule of liquid, etc.

In an embodiment, a composition according to the invention can contain a coating, in particular a gastro-resistant coating or a coating allowing an enteric release of the strain CNCM I-5321.

In an embodiment, the present invention relates to a composition such as defined above, said composition being a pharmaceutical product or a food product, in particular a food supplement.

According to the invention, the term "food supplement" means a food product providing a supplement of nutrients or substances having a nutritional or physiological effect (such as vitamins, minerals, fatty acids or amino acids) lacking or in insufficient quantities in the normal diet of an individual.

In an embodiment, the present invention concerns a composition such as defined above, said composition also comprising at least one element chosen from among the group comprising vitamins, minerals, fatty acids and amino acids.

In a non-limiting manner, the vitamins used in manufacturing food supplements are generally vitamins A, D, E, K, B1, B2, B6, B12 and C, niacin, pantothenic acid, folic acid and biotin.

In a non-limiting manner, the minerals used in manufacturing food supplements are generally chosen from among calcium, magnesium, iron, copper, iodine, zinc, manganese, sodium, potassium, selenium, chromium, molybdenum, fluoride, chloride, phosphorus.

In an embodiment, the present invention concerns a composition such as defined above, said composition also comprising at least one excipient.

In an embodiment, the present invention concerns a composition such as defined above, said composition also comprising at least one flavour.

In an embodiment, the present invention concerns a composition such as defined above, said composition being a drink.

When said strain is present in the form of living bacteria, these are preferably present at a rate of at least $10^5$ ufc per gram of product, advantageously at least $10^6$ ufc per gram, more advantageously at least $10^7$ ufc per gram, and even more advantageously at least $10^8$ ufc per gram.

In an embodiment, the present invention concerns a composition such as defined above, wherein the strain CNCM I-5321 is in association with another probiotic organism, preferably a lactic bacterium.

The following examples describe certain embodiments of the present invention. However, the examples are only presented as an illustration and do not limit in any case, the scope of the invention.

EXAMPLES

Figure 1:
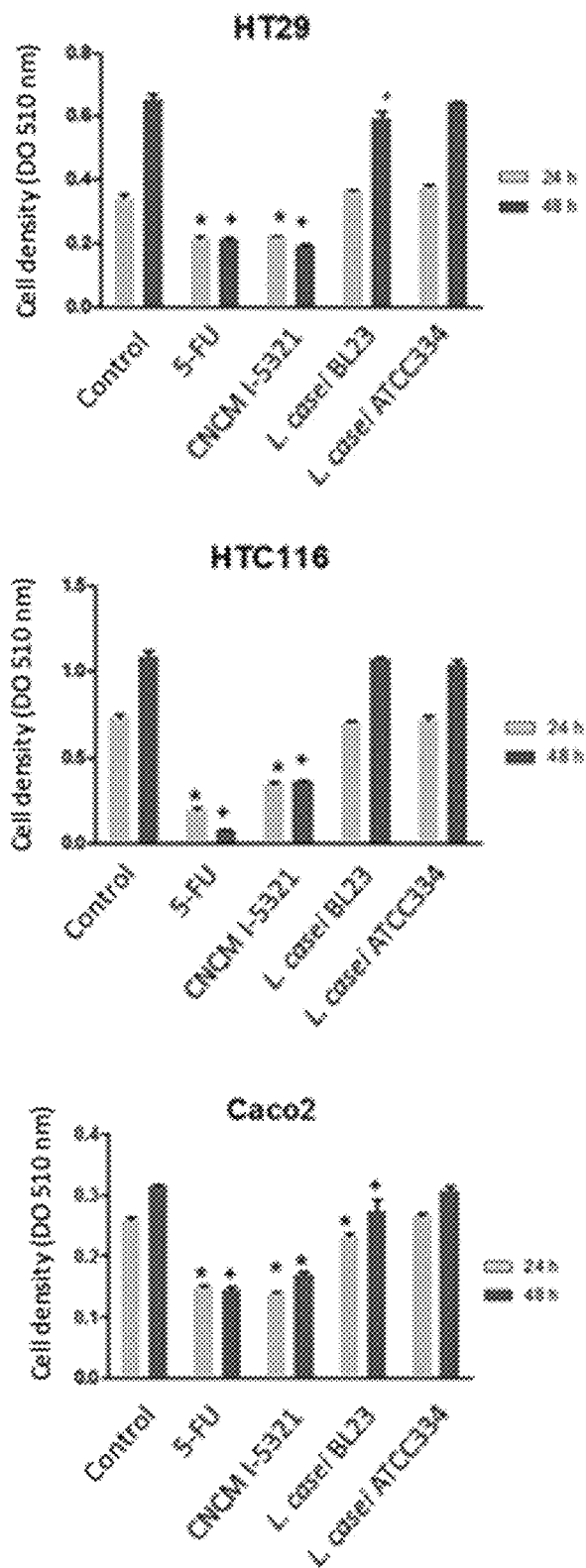
FIG. 1. Antiproliferative effect of the strain CNCM I-5321 on tumour cell lines. The cells HT29, HTC116 and Caco2 are incubated in the presence of PBS (negative control), 5-FU (5 Fluorouracil) (positive control), of the strain CNCM I-5321, of the strain L. casei BL23 and of the strain L. casei ATCC334. * indicates a significant difference with respect to the negative control (P<0.05).

Equipment and Methods
Bacteria

The lactobacilli have been cultivated in a Man-Rogosa-Sharpe (MRS) medium (Difco Laboratories) for one day at 37° C.

For the preparation of cell fractions, the pellet has been washed twice with PBS and a cell extract has been obtained by sonication (10 cycles between 40 and 60 watts of amplitude). The soluble and insoluble components have been separated by centrifugation, the protein content has been quantified by Bradford.

For the preparation of a culture supernatant, the supernatant has been obtained by centrifugation after one night of culture, then sterilisation by filtration (0.45 µm).

For the inactivation of bacteria, the bacteria have been killed by exposure to UV radiation for 15 minutes. The inactivation has been confirmed by incubation on petri dishes.

Cell Lines

All the cell lines have been purchased from ATCC. Cancerous cell lines, HT29, HTC116 and Caco2 have been cultivated in the Eagle medium modified by glucose-rich Dulbecco added to 10% (vol/vol) of foetal bovine serum (FBS), 2 mM of L-glutamine, 50 mg/ml of penicillin and 50 mg/ml of streptomycin in a humidified atmosphere containing 5% of $CO_2$. The non-cancerous cell line FHC has been cultivated in a DMEM/F12 medium added to 10% (vol/vol) of FBS, 2 mM of L-glutamine, 50 mg/ml of penicillin and 50 mg/ml of streptomycin, 0.005 mg/ml of insulin, 0.005 mg/ml of transferrin, 0.00067 mg/ml of hydrocortisone, 20 mg/ml of human epidermic growth factor (EGF) in a humidified atmosphere containing 5% of $CO_2$.

Proliferation Test 24 hours before stimulation, the cells have been developed on 96-well microplates at a rate of $2 \times 10^4$ cells per well. The co-culture with a bacterium ($2 \times 10^6$ cells) has been produced then for 24 and 48 hours. The cells have been fixed in the trichloroacetic acid at 5% (TCA) for 1 hour at 4° C. and washed four times in distilled water. The microplates have been coloured with 100 µl/well of 0.057% (weight/volume) of sulforhodamine powder (SRB)/distilled water, washed four times in acetic acid at 0.1% and re-dehydrated at ambient temperature. The coloured cells have been lysed in the buffer Tris 10 mM and the optic density (OD) has been measured at 510 nm.

Coloration at the Annexin V and Propidium Iodide (PI)

24 hours before stimulation, the cells HT-29 have been seeded at a rate of $1 \times 10^6$ cells/ml and left fixed for one night at 37° C. in a $CO_2$ incubator. The co-culture with a bacterium ($1 \times 10^8$ cells) has been produced for 24 hours. The cells have been collected (trypsinisation) and washed twice with cold PBS, then suspended in the binding buffer 1× at a concentration of $1 \times 10^6$ cells/ml. The cells have been incubated with 5 µl of Annexin V-FITC and 5 µl of PI for 15 minutes at ambient temperature (25° C.) under dark conditions. 400 µl of binding buffer 1× have been added to each tube and the cells have been analysed by flow cytometry. The controls used are (i) untreated cells, and coloured cells with (ii) the annexin V-FITC only, (iii) PI only, and (iv) both the annexin V-FITC and PI.

qPCR Tests

Co-cultures have been produced as indicated above. The RNA has been extracted by using the RNeasy Mini de Qiagen kit. The quality and the concentration of the RNA have been expressed by electrophoresis on agarose gel coloured with ethidium bromide and by spectrophotometric analysis. The DNAc matrix has been synthesised from 1 pg of RNA with the reverse transcription kit High-Capacity cDNA Reverse Transcription Kit (Applied Biosystems). The reaction of RT-qPCR has been achieved in a reactional volume of 25 µl (Takyon™ Rox SYBR® MasterMix dTTP blue) with the following initiators: B-actin, Caspas8, Caspas9, ErbB2, ErbB3, BCL2, BCL-XL in the first qPCR thermal cycle. The expression values have been quantified and standardised by the method ΔCt, by using the geometric average Ct of β-actin as endogenic reference gene.

Results

A test of the antiproliferative activity of the strain CNCM I-5321 has been carried out on different cancer cell lines of the colon, HT-29 (adenocarcinoma of the human colon, type II), HTC116 (human colorectal cancer), and Caco-2 (colorectal adenocarcinoma). The strain CNCM I-5321 is capable of stopping the cell proliferation of human intestinal epithelial lines at a level comparable to that of 5-fluorouracil (5-FU), anti-cancer medicament used here as positive control (FIG. 1).

Figure 2:
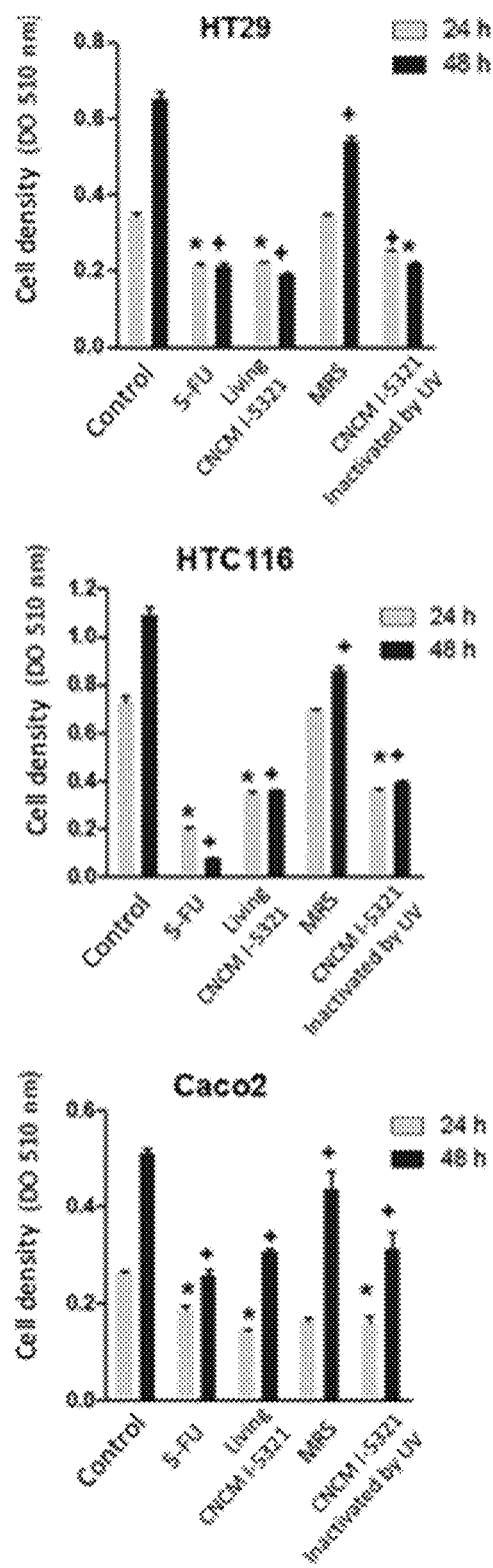
FIG. 2. Antiproliferative effect of the strain CNCM I-5321 inactivated by UV on tumour cell lines. The cells HT29, HTC116 and Caco2 are incubated in the presence of PBS (negative control), 5-FU (5 Fluorouracil) (positive control), of the strain CNCM I-5321, of the culture supernatant of the strain CNCM I-5321 (MRS medium) and of the strain CNCM I-5321 inactivated by UV. * indicates a significant difference with respect to the negative control (P<0.05).
Figure 3:
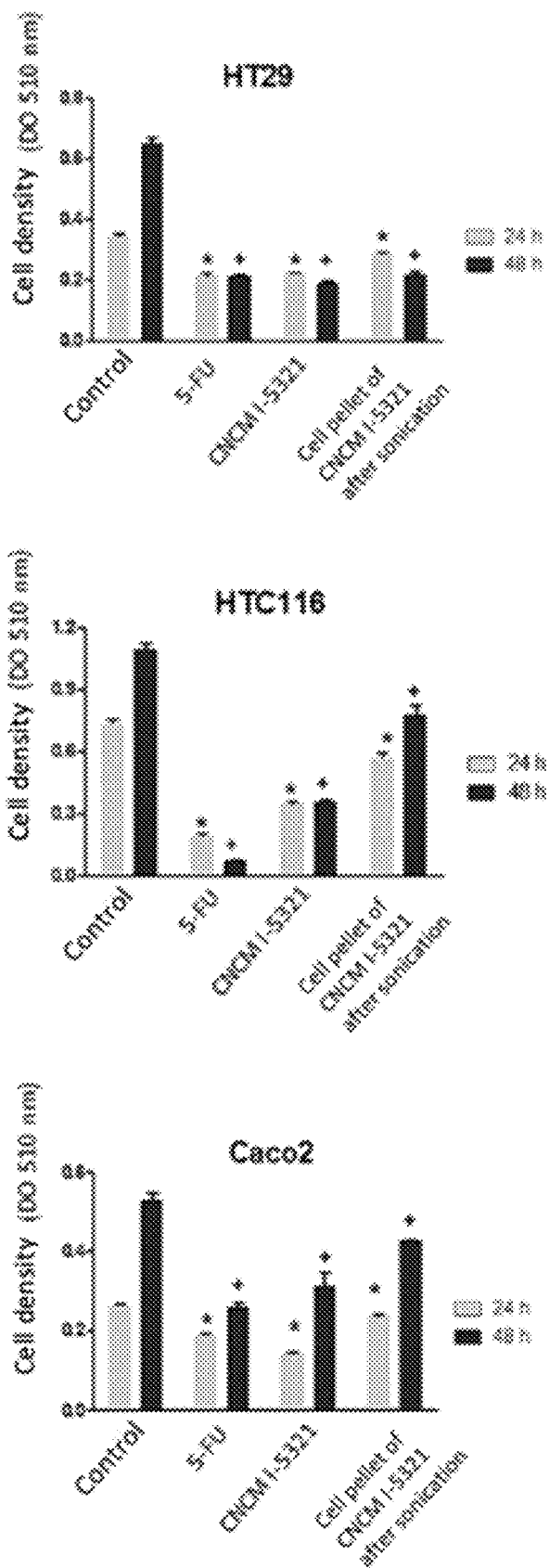
FIG. 3. Antiproliferative effect of the cell pellet of the strain CNCM I-5321 after sonication on the tumour cell lines. The cells HT29, HTC116 and Caco2 are incubated in the presence of PBS (negative control), 5-FU (5 Fluorouracil) (positive control), of the strain CNCM I-5321, of the cell pellet of the strain CNCM I-5321 after sonication. * indicates a significant difference with respect to the negative control (P<0.05).

To determine the mechanism involved in the antiproliferative effect of the strain CNCM I-5321, the culture supernatant (MRS), the cells inactivated by UV, the cells lysed by ultrasound and the living cells have been tested. The supernatant does not show any antiproliferative effect (FIG. 2). However, the cells inactivated by UV and the cells treated by ultrasound have maintained an antiproliferative effect indicating that the strain CNCM I-5321 conserves an antiproliferative effect independently of its viability (FIGS. 2 and 3).

Figure 4:
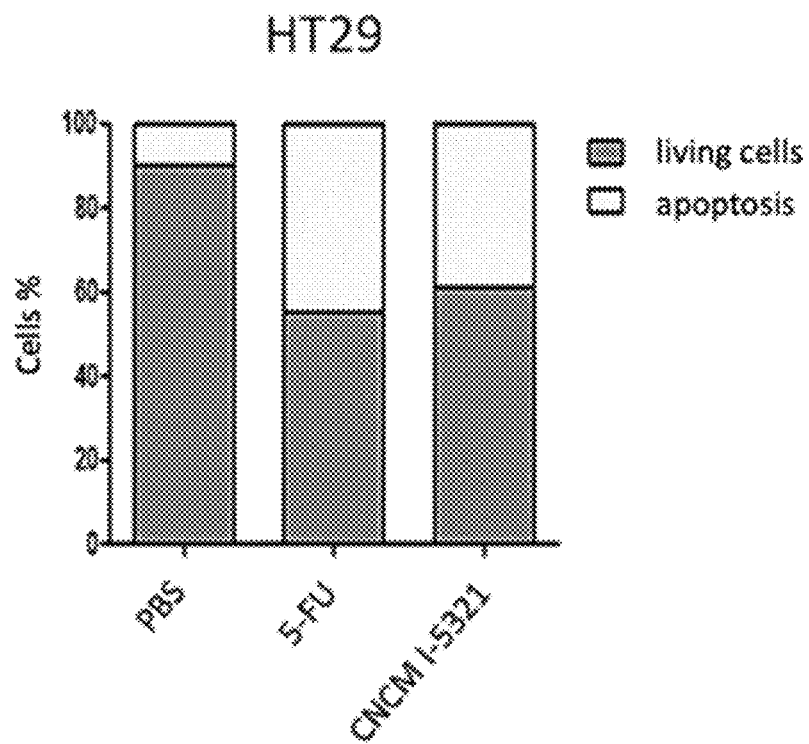
FIG. 4. Proapoptotic effects of the strain CNCM I-5321 on the tumour cell lines. The cells HT29 and HTC116 are incubated for 24 hours with the strain CNCM I-5321. The viability of the cell lines has been determined by coloration with the annexin V-FITC and of propidium iodide (PI) followed by an analysis by flow cytometry.
Figure 4:
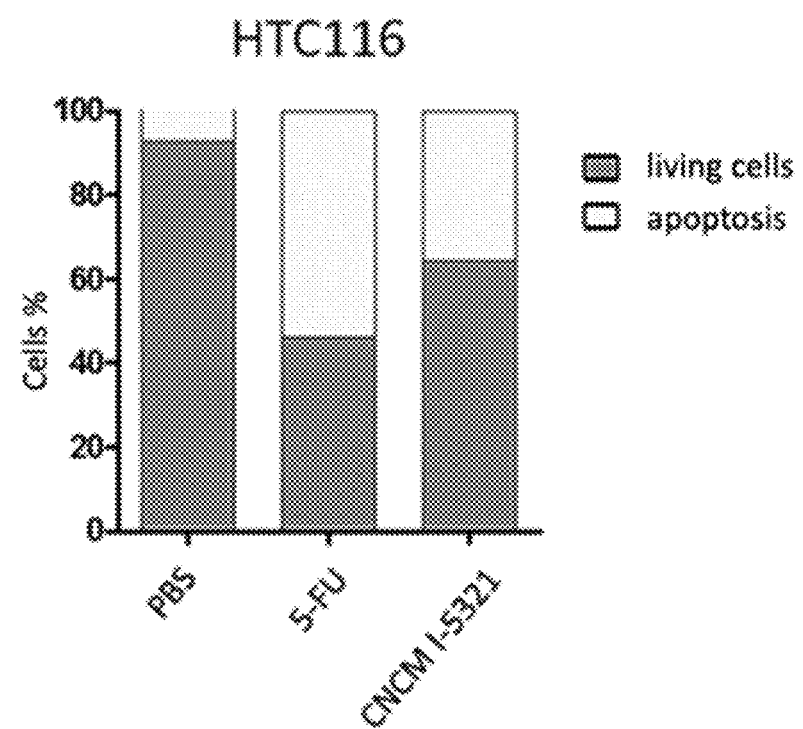
Figure 5:
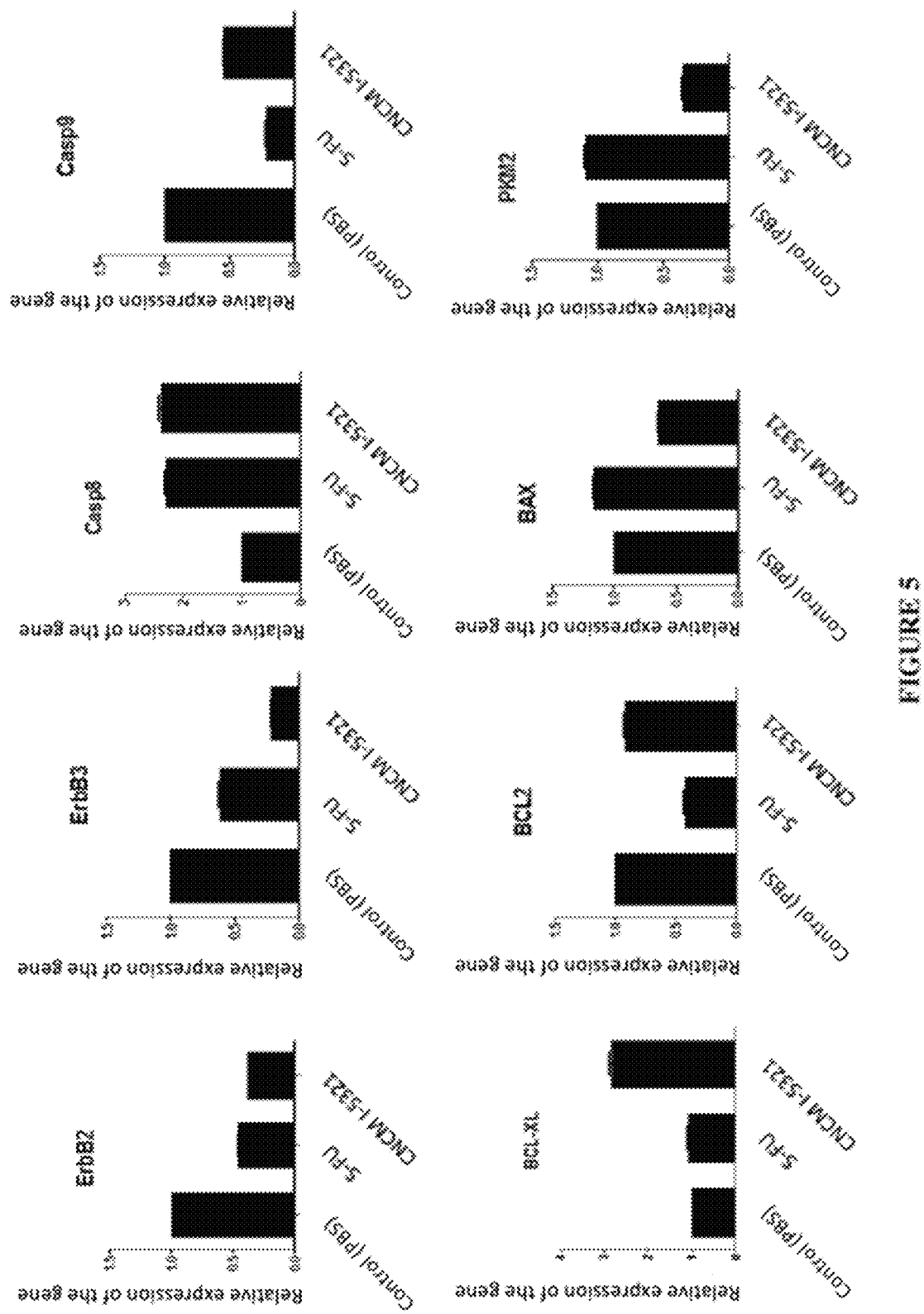
FIG. 5. Expression of the genes erbB2, erbB3, Casp8, Casp9, BCL-XL, BCL2, BAX and PKM2. The values have been calibrated with respect to the expression of the b-actin used as endogenic genic control. The results are presented in the form of relative gene expression (dR) with respect to the expression of the gene in the presence of PBS (negative control).

The strain CNCM I-5321 is also capable of increasing by 25%, the levels of annexin V+/PI+ (late apoptotic cells, FIG. 4) and to induce the apoptotic cell death via the activation and suppression of the expression of antiapoptotic genes ErbB2, ErbB3 (via Casp8), two initiator genes of the apoptosis mediated by TNF-α, and by modulating the expression of the genes BAX and PKM2 involved in the cell metabolism (FIG. 5).

Figure 6:
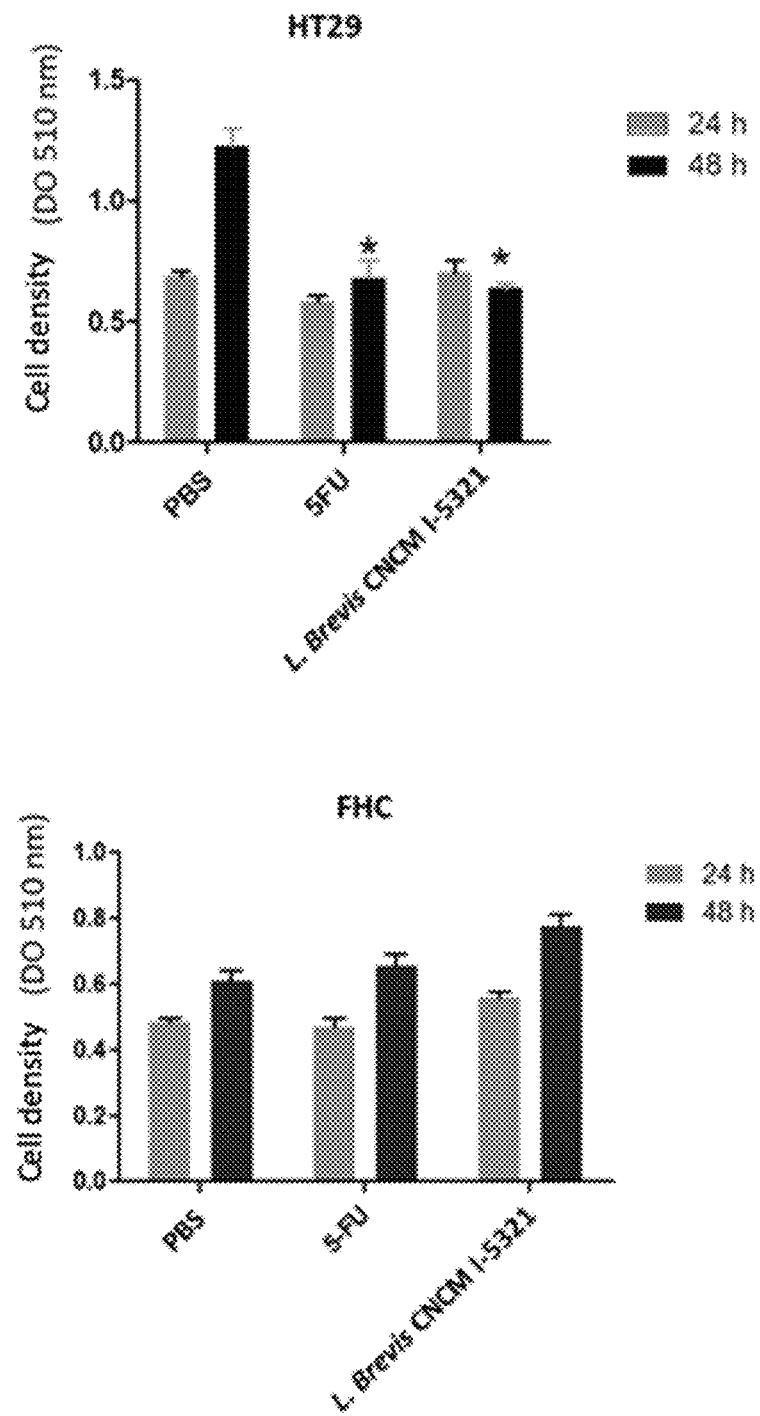
FIG. 6. Specificity of the antiproliferative effect of the strain CNCM I-5321 on the tumour lines. The cancer cells of the colon (line HT29) are incubated in the presence of PBS (negative control), 5-FU (5 Fluorouracil) (positive control), of the strain CNCM I-5321. The noncancerous colon cells (FHC line) are incubated in the presence of PBS (negative control), 5-FU (positive control) and of the strain CNCM I-5321. * indicates a significant difference with respect to the negative control (P<0.05).

To determine if the antiproliferative effect of the strain CNCM I-5321 is specific of the tumour lines, a test of the antiproliferative activity has been carried out on the tumour line HT29 (adenocarcinoma of the human colon, type II) and on the non-cancerous line FHC (foetal human colon cells). The strain CNCM I-5321 inhibits the cell proliferation of the tumour line, but has no significant effect on the growth of non-cancerous cells (FIG. 6).

The invention claimed is:

1. A composition comprising a strain of *Lactobacillus brevis* deposited on 30 May 2018 with the CNCM (French National Collection of Microorganism Cultures) under number I-5321, wherein said strain is present in the form of living bacteria, at a concentration of at least $1 \times 10^5$ colony forming units (CFU) per gram of product.

2. The composition according to claim 1, said composition being a pharmaceutical product or a food product.

3. The composition according to claim 2, wherein the food product is a food supplement.

4. A method of preventing and/or treating a cancer in a subject in need thereof, comprising administering to the subject an effective amount of the composition of claim 1.

5. The method accordingly to claim 4, wherein the cancer is bowel cancer, lung cancer, and liver cancer.

6. The method according to claim 5, wherein the bowel cancer is colorectal cancer.

7. A composition comprising a strain of *Lactobacillus* brevis deposited on 30 May 2018 with the CNCM (French National Collection of Microorganism Cultures) under number I-5321, wherein said strain has been inactivated by exposure to an ultraviolet radiation or by heating, or has been lysed by ultrasound.

8. A method of preventing and/or treating a cancer in a subject in need thereof, comprising administering to the subject an effective amount of the composition of claim 7.

* * * * *